United States Patent [19]
Appel et al.

[11] Patent Number: 6,166,242
[45] Date of Patent: Dec. 26, 2000

[54] METHOD FOR PRODUCING COMPOUNDS CONTAINING FLUORINE, IN PARTICULAR FLUOROBENZALDHYDES AND FLUOROBENZONITRILES

[75] Inventors: Wolfgang Appel; Sergej Pasenok, both of Kelkheim; Thomas Wessel, Frankfurt, all of Germany

[73] Assignee: Aventis Research & Technologies GmbH & Co KG, Germany

[21] Appl. No.: 09/486,517

[22] PCT Filed: Aug. 20, 1998

[86] PCT No.: PCT/EP98/05296

§ 371 Date: Feb. 20, 2000

§ 102(e) Date: Feb. 28, 2000

[87] PCT Pub. No.: WO99/11588

PCT Pub. Date: Mar. 11, 1999

[30] Foreign Application Priority Data

Sep. 2, 1997 [DE] Germany .................. 197 38 196

[51] Int. Cl.$^7$ .................. C07C 255/00; C07C 45/00
[52] U.S. Cl. .................. 558/425; 568/437
[58] Field of Search .................. 558/425; 568/437

[56] References Cited

U.S. PATENT DOCUMENTS 5,466,859 11/1995 Schach et al. .................. 558/425

FOREIGN PATENT DOCUMENTS

| 0265854 | 5/1988 | European Pat. Off. . |
| 0635486 | 1/1995 | European Pat. Off. . |
| 2275426 | 1/1976 | France . |
| 98/05610 | 2/1998 | WIPO . |
| 98/22413 | 5/1998 | WIPO . |

OTHER PUBLICATIONS

Mochizuki Hiromitsu, Ihara Chem. Ind. Co. LTD, *Pat. Abs. of Japan 96*: No 8 of JP 08 092148 (1996).

Ihara Chem. Ind. Co. LTD, Derwent Abstract of JP 5194303, XP–002085380 (1993).

Shin–Akita Kasei KK, Derwent Abstract of JP63 039824, XP–002085381 (1998).

*Primary Examiner*—Cecilia Tsang
*Assistant Examiner*—Joseph Murray
*Attorney, Agent, or Firm*—Connolly Bove Lodge & Hutz LLP

[57] ABSTRACT

The invention concerns a method for producing compound containing fluorine, particularly fluorobenzaldehyde and fluorobenzonitrle, by a halogen exchange reaction with a compound of the formula I as fluorinating agent, defined in the specification, and a quatenary aminophosphonium compound of the formula III as catalyst, as defined in the specification, and in a solvent consisting of a nitro and/or sulfoxy substituted organic compound of the formula IVa and/or IVb, as defined in the specification.

30 Claims, No Drawings

METHOD FOR PRODUCING COMPOUNDS CONTAINING FLUORINE, IN PARTICULAR FLUOROBENZALDHYDES AND FLUOROBENZONITRILES

This application is a 371 of PCT/EP98/05296 filed Aug. 20, 1998.

DESCRIPTION

Process for preparing fluorine-containing compounds, in particular fluorobenzaldehydes and fluorobenzonitriles The present invention relates to a process for preparing fluorine-containing compounds, preferably fluorine-containing aromatic compounds, in particular fluorobenzaldehydes and fluorobenzonitriles, in high purity.

In particular, the invention relates to a process which is improved compared to the prior art and in which fluorination is achieved with high selectivity and in high purity by means of a halogen-fluorine exchange reaction (halex process).

Fluorine-containing compounds are employed, inter alia, in liquid crystal mixtures (EP-A-0 602 596).

The replacement of hydrogen bound to an aromatic ring by fluorine is also very important for the synthesis of bioactive substances or for the preparation of precursors of such compounds.

Furthermore, it is generally known that fluorine has strong and often unexpected effects on the biological activity of chemical compounds. The replacement of hydrogen by fluorine in a biologically active molecule often leads to an analogous compound having increased or modified biological action.

Apart from direct fluorination, the preparation of fluorine compounds by replacement of a halogen (Cl, Br) by fluorine (known as the "halex process") is an extremely valuable reaction which is of great industrial importance.

In the case of aromatic compounds, in particular activated aromatic compounds, the halogen-fluorine exchange proceeds in the form of a nucleophilic substitution.

Carrying out this reaction requires comparatively high temperatures, frequently in the range from 200 to 300° C., as a result of which sometimes considerable amounts of decomposition products are formed. In general, a solvent cannot be dispensed with, so that the space-time yields are significantly lower compared to solvent-free processes.

The halex reaction is frequently accompanied by further secondary reactions which form significant amounts of by-products, especially reductively dehalogenated aromatics, whose removal from the product is extremely difficult and very expensive because of a similarity of boiling points. Owing to these secondary reactions, the applications of the halex reaction are relatively restricted. The specific published prior art is as follows:

D1=U.S. Pat. No. 4,287,374
D2=WO 87/04194
D3=Clark et al., Tetrahedron Letters 28 [1987], 111 ff.
D4=C.A. 109:92451t=JP 63 39,824
D5=JP 05194303 A2 and
D6=JP 08092148 A2.

The use of phase transfer catalysts belongs to the prior art designed to circumvent some of the abovementioned problems. However, other problems such as poor stirrability of the reaction suspension in the case of solvent-free processes remain.

D1 teaches the use of quaternary ammonium or alkylphosphonium salts as phase transfer catalysts. According to D2, pyridinium salts are used as phase transfer catalysts, and D3 uses crown ethers or tetraphenylphosphonium salts as phase transfer catalysts. Some of these phase transfer catalysts have comparatively low activity and are only moderately stable at the temperatures required for carrying out the reaction.

D4 proposes carrying out the chlorine-fluorine exchange in the presence of polymerization inhibitors such as dinitrobenzene. However, the use of dinitrobenzene unfortunately has some serious disadvantages. As has recently become known, dinitrobenzene reacts with KF with replacement of $NO_2$ and formation of nitrite anions which leads to the formation of phenol derivatives and consumption of additional amounts of fluorination reagents.

According to D5, the chlorine-fluorine exchange reaction is carried out in nitrobenzene as solvent, so that the space-time yield is considerably lower compared to solvent-free processes. In addition, the separation of the products from nitrobenzene can be difficult, particularly in the case of compounds having similar boiling points.

D6 discloses a procedure in which the dehalogenation of monochlorinated benzaldehydes during the halex reaction is reduced. 4-Chloro-benzaldehyde is reacted with sulfolane, KF and tetraphenylphosphonium bromide in the presence of nitrobenzene or nitronaphthalene. Although this reduces the rate of formation of the by-product benzaldehyde, the amount formed is still too high at 0.72% after 3 hours. In addition, the removal of the dehalogenation products from the desired fluorinated target products is generally difficult because of very similar boiling points.

In view of the prior art indicated and discussed above, it is an object of the invention to provide a process of the type mentioned at the outset which allows the preparation of defined target compounds in good yield with high selectivity and in high purity. The new process should be able to be used industrially and be able to be implemented inexpensively with very little environmental pollution and using relatively simple means. In particular, the process should be very largely free of the abovementioned disadvantages from which the prior art processes have previously suffered.

A further object of the invention is to improve the halex reaction so that dehalogenation is very substantially suppressed.

These objects and also further objects which are not listed in more detail but can be derived or deduced from the introductory discussion of the prior art are achieved by a process of the type mentioned at the outset having the features of claim 1. Advantageous modifications of the process of the invention are claimed in the subordinate claims dependent on claim 1.

In a process for preparing fluorine-containing compounds, reacting a compound containing one or more halogen atoms which can be replaced by fluorine with a fluoride of the formula I or a mixture of fluorides of the formula I

where $KAT^+$ is an alkali metal ion, $NH_4^+$, an alkaline earth metal ion or a cation of the formula II

where $A^1$, $A^2$, $A^3$, $A^4$ are, independently of one another, identical or different and are each straight-chain or branched alkyl or alkenyl having from 1 to 12 carbon atoms, cycloalkyl having from 4 to 8 carbon atoms, aryl having from 6 to 12 carbon atoms or aralkyl having from 7 to 12 carbon atoms, in the presence of a compound or a mixture of compounds of the formula III

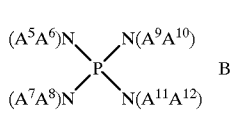  (III)

where $A^5, A^6, A^7, A^8, A^9, A^{10}, A^{11}, A^{12}$ are, independently of one another, identical or different and are each straight-chain or branched alkyl or alkenyl having from 1 to 12 carbon atoms, cycloalkyl having from 4 to 8 carbon atoms, aryl having from 6 to 12 carbon atoms, aralkyl having from 7 to 12 carbon atoms, or $A^5 A^6, A^7 A^8, A^9 A^{10}, A^{11}, A^{12}$ are, independently of one another, identical or different and are bound to one another either directly or via O or N—$A^{13}$ to form a ring having from 3 to 7 ring atoms, $A^{13}$ is alkyl having from 1 to 4 carbon atoms and $B^-$ is a monovalent acid anion or the equivalent of a polyvalent acid anion, and in the presence of one or more compounds of the formulae IV encompassing IVa and/or IVb $$X\text{—}NO_2 \qquad (IVa),$$
$$X\text{—}SO\text{—}X' \qquad (IVb),$$

where X and X' are, independently of one another, identical or different and are each substituted or unsubstituted $(C_6-C_{18})$-aryl, substituted or unsubstituted $(C_5-C_{18})$-aryloxy, substituted or unsubstituted $(C_5-C_{18})$-arylthio, substituted or unsubstituted $(C_7-C_{12})$-aralkyl or a radical of the formula V

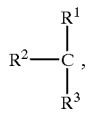  (V)

where $R^1, R^2, R^3$ are, independently of one another, identical or different and are each hydrogen, straight-chain or branched alkyl or alkenyl having from 1 to 12 carbon atoms, cycloalkyl having from 4 to 8 carbon atoms, aryl, substituted aryl, aryloxy, arylthio, each having from 6 to 18 carbon atoms, or aralkyl having from 7 to 12 carbon atoms, in the presence or absence of a solvent at temperatures in the range from 40° C. to 260° C. makes it possible to provide, particularly advantageously, a process which improves the known processes in respect of selectivity and the quality of the resulting process products in a manner which could not readily have been foreseen.

Alkali metal ion is lithium, sodium, potassium, rubidium and/or cesium, in particular sodium and/or potassium, very particularly potassium;

alkaline earth metal ion is magnesium, calcium, strontium and/or barium, in particular calcium;

alkyl having from 1 to 4 carbon atoms encompasses straight-chain or branched radicals such as methyl, ethyl, n-propyl, isopropyl, n-butyl and tert-butyl.

Straight-chain alkyl or alkenyl having from 1 to 12 carbon atoms encompasses, inter alia, unbranched, saturated hydrocarbon radicals such as methyl, ethyl, propyl, butyl, pentyl, hexyl, heptyl, octyl, nonyl, decyl, undecyl and dodecyl, and also unbranched, unsaturated hydrocarbon radicals such as vinyl, allyl, 2-butenyl, 2-pentenyl and 2-decenyl.

Straight-chain or branched alkyl or alkenyl having from 1 to 12 carbon atoms encompasses, inter alia, the abovementioned straight-chain alkyls or alkenyls and also branched radicals such as isopropyl, 2-butyl, 2-methylpropyl, tert-butyl, 2-methylbutyl, 1,1-dimethylpropyl, 1,1,3,3-tetramethylbutyl and 2-decyl.

Cycloalkyl having from 4 to 8 carbon atoms is cyclobutyl, cyclopentyl, cyclohexyl, cycloheptyl or cyclooctyl, preferably cyclohexyl, cycloheptyl or cyclooctyl, very particularly preferably cyclohexyl.

For the purposes of the present invention, the expression "aryl" refers to a cyclic aromatic radical having from 6 to 18, in particular from 6 to 14, carbon atoms, very particularly preferably from 6 to 12 carbon atoms, for example phenyl, naphthyl or biphenyl, preferably phenyl.

Unsubstituted or substituted $(C_6-C_{18})$-aryl encompasses firstly unsubstituted aryls as mentioned above; these can be monosubstituted or polysubstituted by up to 3 substituents; possible substituents are essentially: F, $NO_2$ (not in the case of compounds of the formulae I, II, III), $CF_3$, CN, CHO, COF, $SO_2F$, $OCF_3$, $SOCF_3$, $SO_2CF_3$, COOR, CONRR', $SO_2R$, COR or OR or a —OC—NR—CO— or —OC—O—CO— group which links two ortho positions, where R and R' are, independently of one another, identical or different and are each hydrogen, a straight-chain or branched alkyl group having from 1 to 4 carbon atoms, an aryl group having from 6 to 12 carbon atoms or an aralkyl group having from 7 to 12 carbon atoms, monosubstituted to trisubstituted by fluorine atoms, and R and R' may be joined to form a three- to seven-membered ring;

substituted or unsubstituted $(C_6-C_{18})$-aryloxy encompasses firstly aryloxy having from 6 to 18 carbon atoms, preferably isocyclic compounds; the unsubstituted aryloxy radicals are, for example, phenoxy or 1- or 2-naphthyloxy; these may, like the substituted aryls, bear appropriate radicals as substituents;

substituted or unsubstituted $(C_6-C_{18})$-arylthio encompasses firstly thioaryls having from 6 to 18 carbon atoms, particularly preferably isocyclic compounds; the substituted arylthio radicals are, for example, phenylthio or 1- or 2-naphthylthio; these may, like the substituted aryls, bear appropriate radicals as substituents; substituted or unsubstituted $(C_7-C_{12})$-aralkyl encompasses aralkyls having from 7 to 12 carbon atoms; these include, inter alia, benzyl, 2-phenylethyl, 1-phenylethyl, 1-methyl-1-phenylethyl, 3-phenylpropyl, 4-phenylbutyl, 2-methyl-2-phenylethyl or 1-methylnaphthyl or 2-methylnaphthyl. As regards the possible substitution, these groups may bear substituents on the ring and/or side groups; possible substituents on the ring are, inter alia, up to three of the following radicals: F, $NO_2$ (not in the case of compounds of the formulae I, II, III), $CF_3$, CN, CHO, COF, $SO_2F$, $OCF_3$, $SOCF_3$, $SO_2CF_3$, COOR, CONRR', $SO_2R$, COR or OR or a —OC—NR—CO— or —OC—O—CO— group which links two ortho positions, where R and R' are, independently of one another, identical or different and are each hydrogen, a straight-chain or branched alkyl group having from 1 to 4 carbon atoms, an aryl group having from 6 to 12 carbon atoms or an aralkyl group having from 7 to 12 carbon atoms, monosubstituted to trisubstituted by fluorine atoms, and R and R' may be joined to form a three- to seven-membered ring;

In particular and inter alia, the process of the invention combines a number of extraordinary advantages:

It is surprising that the use of the compound of the formulae IV (as additive to the reaction mixture for the chlorine-fluorine exchange reaction) together with the phase transfer catalysts of the formula III enables the formation of undesirable by-products (especially reductively dehalogenated aromatics) to be suppressed or completely avoided.

Inter alia, the addition of compounds of the formulae IV in combination with compounds of the formula III as additive for the chlorine-fluorine exchange reaction is therefore, looked at overall, an environmentally friendly chemical process.

The compounds of the formulae IV and III can, as solids or liquids, cover a wide range of melting points or boiling points, so that appropriate selection of a suitable compound as a function of the boiling point of the expected target product in virtually all cases enables a work-up of the reaction mixture after fluorination by fractionation of the reaction mixture by distillation.

This also makes it possible to isolate the compounds of the formulae IV and/or III and to recycle them.

The nitro and thioxo compounds of the formulae IV can, in the context of the invention, provide these advantages when they are present in the reaction mixture, i.e. they are an addition to the reaction mixture for fluorination by means of halogen exchange. The proportion of compounds of the formulae IV is variable, since even small additions are able to exert an overall positive influence on the halex reaction.

The compounds of the formulae IV and III which may be used according to the invention as additives are frequently very cheap and most of them are commercially available and therefore accessible. Compounds of the formula IV or III which are not commercially available can be synthesized in a simple manner by methods with which those skilled in the art are familiar.

The advantageous effects achievable by means of the invention are obtained when a compound of the formula IVa and/or IVb or a mixture of a plurality of compounds of the formulae IV (encompassing the formulae IVa and/or IVb), in each case together with at least one catalyst of the formula III, are added in the halex reaction.

The amount of compounds of the formulae IV which are used according to the invention can vary over a wide range. In general, quite useful results can be achieved when use is made of, based on the compound containing halogen to be replaced, from about 0.1 to 20% by weight. If the amount is less than 0.1%, the reduction in the occurrence of dehalogenation products is not pronounced enough. If the amount of compounds of the formulae IV is above 20% by weight, generally no measurable better effect than when using smaller additions is achieved. Preference is given to additions in the range from 0.5 to 10% by weight. The process of the invention is particularly advantageously carried out in the presence of from 1 to 5% by weight of one or more compounds of the formulae IVa and/or IVb, based on the weight of the starting materials (compounds containing replaceable halogen).

The compounds of the formulae IV which contain two or more nitro groups, two or more thioxo groups, one nitro group and one thioxo group, one nitro group and a plurality of thioxo groups or one thioxo group and a plurality of nitro groups can be added in smaller amounts compared to mononitro derivatives or monothioxo compounds. Here, a proportion of 0.1–10% by weight, preferably 0.5–8% by weight, in particular 1–5% by weight, based on the starting materials used, is advantageous.

The nitro compounds of the formula IVa and the thioxo compounds of the formula IVb essentially encompass aromatic compounds and aliphatic compounds. The aromatic compounds may in turn be substituted on the ring by nitro and/or thioxo groups; the nitro and/or thioxo group(s) may also be located in a side group of the aromatic compound.

The aromatic compounds used for the purposes of the invention include nitro compounds of the formula IVa and/or thioxo compounds of the formula IVb in which X is unsubstituted or substituted $(C_6-C_{18})$-aryl, substituted or unsubstituted $(C_6-C_{18})$-aryloxy, substituted or unsubstituted $(C_6-C_{18})$-arylthio or substituted or unsubstituted $(C_7-C_{12})$ aralkyl.

Among these, preference is given to unsubstituted or substituted aryls having from 6 to 8 carbon atoms, unsubstituted or substituted aryloxy radicals having from 6 to 8 carbon atoms, unsubstituted or substituted arylthio radicals having from 6 to 8 carbon atoms and unsubstituted or substituted aralkyls having from 8 to 10 carbon atoms.

Of very particular interest are unsubstituted or substituted nitroaryls having from 6 to 8 carbon atoms and unsubstituted or substituted nitroaryloxy compounds having from 6 to 8 carbon atoms.

Among the aliphatic nitro compounds and/or thioxo compounds, particular mention may be made in the context of the invention of those in which the radical X in the formula IV is a radical of the formula V

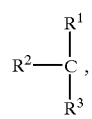

(V)

where $R^1, R^2, R^3$ are, independently of one another, identical or different and are each hydrogen, straight-chain or branched alkyl or alkenyl having from 1 to 12 carbon atoms or cycloalkyl having from 4 to 8 carbon atoms.

It is particularly advantageous to use compounds of the formulae IV in which the radical X is a radical of the formula V in which $R^1$, $R^2, R^3$ are, independently of one another, identical or different and are each hydrogen, straight-chain or branched alkyl having from 1 to 4 carbon atoms or cycloalkyl having from 5 to 7 carbon atoms, preferably cyclohexyl.

Preferred compounds to be used according to the invention include, inter alia, nitrobenzene, 2-fluoronitrobenzene, 3-fluoronitrobenzene, 4-fluoronitrobenzene, 2,4-difluoronitrobenzene, 3-chloronitrobenzene, 2-nitrotoluene, 3-nitrotoluene, 4-nitrotoluene, 2-nitroanisole, 3-nitroanisole, 4-nitroanisole, 2-nitrothiophene, 4-nitro-2-propylbenzene, 1-nitronaphthalene, 2-nitronaphthalene, 2,4-dinitrobiphenyl, 4,4'-dinitrobiphenyl, bis(4-nitrophenyl) ether, bis(nitrophenyl)disulfide, nitromethane, nitroethane, nitropropane, nitroanthracene, 1-nitropyrene, dimethyl sulfoxide, diphenyl sulfoxide, phenyl methyl sulfoxide, diethyl sulfoxide and/or methyl trifluoromethyl sulfoxide.

Owing to their favorable price and their universal availability, nitrobenzene and/or dimethyl sulfoxide (DMSO) are very particularly preferred.

A great advantage of the process of the invention is its universal applicability to many substrates which contain one or more halogen atoms which can be replaced by fluorine.

Here, the term "halogen which can be replaced by fluorine" means chlorine, bromine or iodine, in particular chlorine or bromine, preferably chlorine, which can be replaced by fluorine in a nucleophilic substitution using fluoride.

The range of substrates which can be reacted according to the invention in the presence of compounds of the formulae III and IVa and/or IVb is extremely broad and comprehensive.

Thus, preference is given to using, as compound containing halogen which can be replaced by fluorine, an aromatic compound having from 0 to 3 nitrogen atoms in the ring and substituted on the ring by chlorine or bromine substituents, in particular chlorine substituents, which can be replaced by fluorine and may be substituted on the ring by at least one further substituent which promotes nucleophilic substitution of aromatic compounds.

The process of the invention is equally readily applicable to aromatic or heteroaromatic compounds. Likewise possible is the fluorination of cyclic compounds having only one ring or of fused cyclic compounds and heterocyclic compounds. Without making any claim to completeness, preferred starting compounds are ones which have one or more halogen atoms which can be replaced by fluorine and are of the benzene, naphthalene, pyridine, anthracene, phenanthrene, pyrimidine or pyrazine type or are benzofused ring systems based on pyridine (quinoline, isoquinoline, acridine, acridone type), on pyrimidine, pyrazine and piperazine (benzodiazines of the cinnoline, phthalazine, quinazoline, quirioxaline, phenazine, phenoxazine type). It is likewise possible to use derivatives which may have at least one further substituent which promotes nucleophilic substitution of aromatic compounds. This further substituent which promotes nucleophilic substitution of aromatic compounds usually leads to an activation of the aromatic compound which aids a halogen-fluorine exchange reaction.

The further substituents which promote nucleophilic substitution of an aromatic compound are I and M substituents which reduce the electron density or nucleophilicity of the aromatic and thereby hinder electrophilic substitution. However, the aromatic is thereby activated with regard to nucleophilic substitution. The activating effect of these substituents is particularly great when they are in the ortho or para position relative to the halogen to be replaced by fluorine.

In a useful embodiment, the reaction is carried out using an aromatic compound which bears on the ring a halogen atom which can be replaced by fluorine and has at least one further substituent selected from the group consisting of F, Cl, Br, I, $CF_3$, CN, CHO, COF, COCl, $SO_2F$, $SO_2Cl$, $OCF_3$, $SOCF_3$, $SO_2CF_3$, COOR, CONRR', $SO_2R$, COR or OR or an —OC—NR—CO— or an —OC—O—CO— group which links two ortho positions, where R and R' are, independently of one another, identical or different and are each hydrogen, a straight-chain or branched alkyl group having from 1 to 4 carbon atoms, an aryl group having from 6 to 12 carbon atoms or an aralkyl group having from 7 to 12 carbon atoms and the alkyls and aralkyls may bear from 1 to 3 halogen substituents, and R and R' may be joined to form a three- to seven-membered ring.

It is also possible to use an aromatic compound which bears on the ring a halogen substituent which can be replaced by fluorine and has at least one further substituent selected from the group consisting of F, Cl, Br, I, $CF_3$, CN, CHO, COF, COCl, $SO_2F$, $SO_2Cl$, $OCF_3$, $SOCF_3$, $SO_2CF_3$, COOR, CONRR', $SO_2R$, COR or OR or an —OC—NR—CO— or —OC—O—CO— group which links two ortho positions, where R and R' are, independently of one another, identical or different and are each hydrogen, a straight-chain or branched alkyl group having from 1 to 6 carbon atoms, an aryl group having from 6 to 12 carbon atoms or an aralkyl group having from 7 to 12 carbon atoms and the alkyls and aralkyls may bear from 1 to 3 halogen substituents.

The abovementioned aromatic compounds can also have additional substituents, for example alkyl radicals, amino groups, alkylamino groups, hydroxyl groups or alkoxy groups.

The starting substrate used can also be an aromatic compound which is substituted on the ring by a halogen substituent capable of being replaced by fluorine and bears at least one further halogen substituent which can be replaced by fluorine and, if desired, a further substituent selected from the group consisting of F, $CF_3$, CN, CHO, COF, COCl, $SO_2F$, $SO_2Cl$, $OCF_3$, $SOCF_3$, $SO_2CF_3$, COOR, CONRR', $SO_2R$, COR or OR or an —OC—NR—CO— or —OC—O—CO— group which links two ortho positions. These starting compounds accordingly have at least two halogen atoms which can be replaced by fluorine. These substrates are usually capable of a single or double halogen-fluorine exchange without them having to have a further substituent selected from the abovementioned group. They can, however, also have a further substituent from the group of abovementioned radicals which favors nucleophilic substitution of aromatic compounds. The presence of the substituents increases the reactivity of the aromatic compound in respect of the halogen-fluorine exchange reaction.

The incorporation of at least one nitrogen atom in the aromatic ring increases the reactivity of the aromatic compound so that halogen-fluorine exchange may be able to take place even without the presence of a further substituent which promotes nucleophilic substitution of the aromatic compound.

Good results are also obtained according to the invention when using compounds of the formula VI

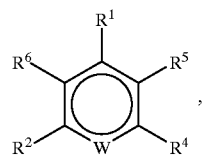

(VI)

where W is N or C—$R^3$, one of the radicals $R^1$, $R^2$, $R^4$, $R^5$, $R^6$ and possibly $R^3$ is F, Cl, $CF_3$, CN, CHO, COF, COCl, $SO_2F$, $SO_2Cl$, $OCF_3$, $SO_2CF_3$, COOR, CONRR', $SO_2R$, COR or OR or two of the radicals which are in ortho positions relative to one another are —CO—O—CO— or —CO—NR—CO—, where R and R' are, independently of one another, identical or different and are each hydrogen, a straight-chain or branched alkyl group having from 1 to 6 carbon atoms, an aryl group having from 6 to 12 carbon atoms or an aralkyl group having from 7 to 12 carbon atoms, one further radical from among $R^1$, $R^2$, $R^4$, $R^5$, $R^6$ and possibly $R^3$ is halogen and the other radicals are hydrogen, F or Cl.

The groups —CO—O—CO— and —CO—NR—CO— are generally two of the radicals $R^1$ to $R^6$ which are in ortho positions relative to one another, in particular two radicals from the group $R^1$, $R^2$, $R^4$, $R^5$, $R^6$ in ortho positions relative to one another if W is N or two radicals from the group $R^2$, $R^3$ and $R^4$ in ortho positions relative to one another if W is C—$R^3$.

In the compound of the formula VI, one of the radicals $R^1$, $R^2$, $R^4$, $R^5$, $R^6$ and possibly $R^3$ or the radical $R^3$ is, in particular, F, Cl, $CF_3$, CN, CHO, COF, COCl, $OCF_3$, COOR, CONRR', COR, OR, —CO—O—CO— or —CO—NR—CO—, preferably Cl, F, $CF_3$, CN, CHO, COOR or COCl; R and R' are, in particular, hydrogen, a straight-chain or branched alkyl having from 1 to 4 carbon atoms or aryl having from 6 to 12 carbon atoms, preferably hydrogen or straight-chain or branched alkyl having from 1 to 3 carbon atoms, particularly preferably methyl or ethyl; one or two of the radicals $R^1$, $R^2$, $R^4$, $R^5$, $R^6$ and possibly $R^3$ are halogen and the remaining radicals are identical or different and are H or F.

A particularly preferred group of substrates which gives very good results in the process of the invention is the group consisting of substituted benzaldehydes and benzonitriles. Among these, very particular preference is in turn given to 2-chlorobenzaldehyde, 3-chlorobenzaldehyde, 4-chlorobenzaldehyde, 2-bromobenzaldehyde, 3-bromobenzaldehyde, 4-bromobenzaldehyde, 2,3-dichlorobenzaldehyde, 2,4-dichlorobenzaldehyde, 2,6-dichlorobenzaldehyde, 3,5-dichlorobenzaldehyde, 2,4,6-trichlorobenzaldehyde, 2-chlorobenzonitrile, 3-chlorobenzonitrile, 4-chlorobenzonitrile, 2-bromobenzonitrile, 3-bromobenzonitrile, 4-bromobenzonitrile, 2,3-dichlorobenzonitrile, 2,4-dichlorobenzonitrile, 2,6-dichlorobenzonitrile, 3,5-dichlorobenzonitrile and 2,4,6-trichlorobenzonitrile as substrate.

To carry out the reaction according to the invention, use is made of a fluoride of the formula I or a mixture of fluorides of the formula I $$KAT^+F^- \qquad (I)$$

where $KAT^+$ is an alkali metal ion, $NH_4^+$, an alkaline earth metal ion or a cation of the formula II $$A^1A^2A^3A^4N^+ \qquad (II)$$

where $A^1$, $A^2$, $A^3$, $A^4$ are, independently of one another, identical or different and are each straight-chain or branched alkyl or alkenyl having from 1 to 12 carbon atoms, cycloalkyl having from 4 to 8 carbon atoms, aryl having from 6 to 12 carbon atoms or aralkyl having from 7 to 12 carbon atoms.

In this context, preference is given to using calcium fluoride, ammonium fluoride, lithium fluoride, sodium fluoride, potassium fluoride, rubidium fluoride, cesium fluoride or a mixture thereof, in particular lithium fluoride, sodium fluoride, potassium fluoride, rubidium fluoride, cesium fluoride or a mixture thereof, advantageously sodium fluoride, potassium fluoride, cesium fluoride or a mixture thereof, particularly preferably potassium fluoride and/or cesium fluoride. It is frequently sufficient to use potassium fluoride as sole fluoride.

Among the cations of the formula II, it is in turn particularly advantageous to use those which make possible fluorination by means of the halex reaction using one or more compounds selected from the group consisting of tetramethylammonium fluoride, tetraethylammonium fluoride, tetrapropylammonium fluoride, tetra(n-butyl)ammonium hydrogen fluoride and/or tetraphenylammonium fluoride. Tetramethylammonium fluoride and/or tetraphenylammonium fluoride are particularly useful.

For the purposes of the invention, the fluorinating agents of the formula I are used in an amount which is sufficient to achieve the desired degree of halogen exchange. Preference is given to using them in a stoichiometric amount based on the amount of starting compound. Preference is also given to using them in excess, particularly preferably a 1.1- to 2.0-fold molar amount based on the number of moles of halogen atoms to be replaced in the starting compound or compounds.

As regards the ratio of amounts, it does, however, need to be taken into account that there can be cases in which an excess of fluoride can lead to undesirable by-products. In these cases, it can also be advisable to use a deficiency of the fluorides of the formula I.

The ratio fluoride of the formula I: equivalents of halogen atoms to be replaced is usually (0.5 to 10):1, in particular (0.8 to 5):1, particularly preferably (1 to 1.5):1.

As already mentioned at the outset, the reaction is carried out in the presence of a compound of the formula III which functions as catalyst.

The compounds of the formula III can be prepared, for example, by reaction of phosphorus pentachloride with dialkylamines. However, phosphorus pentachloride can also be reacted stepwise with different secondary amines, for example dialkylamines, in order to obtain unsymmetrically substituted compounds of the formula III. Further possible ways of synthesizing compounds of the formula III are described by R. Schwesinger et al., Angew. Chemie 103 (1991) 1376 and R. Schwesinger et al., Chem. Ber. 127 (1994) 2435 to 2454. The compounds are therefore readily obtainable by methods known to those skilled in the art.

It is useful to employ a compound of the formula III in which $A^5$, $A^6$, $A^7$, $A^8$, $A^9$, $A^{10}$, $A^{11}$, $A^{12}$ are, independently of one another, identical or different and are straight-chain or branched alkyl or alkenyl, in particular alkyl, having from 1 to 12 carbon atoms, in particular from 1 to 8 carbon atoms, preferably from 1 to 4 carbon atoms, or cycloalkyl having from 4 to 8 carbon atoms, in particular 5 to 6 carbon atoms. These compounds are of particular interest since they can be prepared in a comparatively simple manner starting from the corresponding dialkylamines, dialkyleneamines, dicycloalkylamines or secondary amines containing one alkyl radical and one alkenyl radical, one alkyl radical and one cycloalkyl radical or one alkenyl radical and one cycloalkyl radical.

Examples of alkyl are methyl, ethyl, n-propyl, i-propyl, n-butyl, i-butyl, n-pentyl, 3-methylbutyl, n-hexyl, 2-ethylhexyl, in particular methyl, ethyl, n-propyl, n-butyl, while examples of alkenyl are allyl, prop-2-enyl, n-but-2-enyl;, and examples of cycloalkyl are cyclopentyl, cyclohexyl, 4-methylcyclohexyl and 4-tert-butylcyclohexyl.

It can also be advantageous to use a compound of the formula III in which $A^5A^6=A^7A^8$ or $A^5A^6=A^7A^8=A^9A^{10}$ or $A^5A^6=A^7A^8=A^9A^{10}=A^{11}A^{12}$. These compounds in which two or more of the groups $A^5A^6$, $A^7A^8$, $A^9A^{10}$ and $A^{11}A^{12}$ are identical to one another are relatively easily obtainable.

It is also possible to use a compound of the formula III in which $A^5=A^6$, $A^7=A^8$, $A^9=A^{10}$ and/or $A^{11}=A^{12}$. These compounds are comparatively readily obtainable and are therefore of some interest.

In a further preferred embodiment, the process of the invention is carried out using a compound of the formula III in which $A^5=A^6=A^7=A^8$ or $A^5=A^6=A^7=A^8=A^9=A^{10}$ or $A^5=A^6=A^7=A^8A^9=A^{10}=A^{11}=A^{12}$. The abovementioned compounds in which four, six or eight of the radicals $A^5$ to $A^{12}$ are identical are likewise of importance because of their availability.

In another modification of the process of the invention, use is made of a compound of the formula III in which $A^5A^6$ or $A^5A^6$ and $A^7A^8$ or $A^5A^6$ and $A^7A^8$ and $A^9A^{10}$ or $A^5A^6$ and $A^7A^8$ and $A^9A^{10}$ and $A^{11}A^{12}$ are joined to one another either directly or via O or N—$A^{13}$ to form a saturated or unsaturated ring having 5 or 6 ring atoms. Accordingly, these compounds contain one, two, three or four of the rings described further above.

In addition, it can be advantageous in the process claimed to use a compound of the formula in which $A^5A^6$ or $A^7A^8$ and $A^9A^{10}$ or $A^5A^6$ and $A^7A^8$ and $A^9A^{10}$ or $A^5A^6$ and $A^7A^8$ and $A^9A^{10}$ and $A^{11}A^{12}$ are joined to form a ring which includes, as ring members the N atom on which the respective radicals $A^5$ to $A^{12}$ are located and possibly O or N—$A^{13}$ and $CH_2$ groups. In this group of substances, the N atoms together with the radicals $A^1$ to $A^8$ located on them in each case form, for example, a hexahydropyridine ring, tetrahydropyrrole ring, a hexahydropyrazine ring or a morpholine ring. Accordingly, these compounds contain one, two, three or four of the above-described rings.

In the compound of the formula III, $B^-$ is, as already mentioned at the outset, a monovalent acid anion or the equivalent of a polyvalent acid anion, in particular the anion of an inorganic mineral acid, an organic carboxylic acid, an aliphatic or aromatic sulfonic acid.

It is usual to use a compound of the formula III in which $B^-$ is $F^-$, $Cl^-$, $Br^-$, $I^-$, $HF_2^-$, $BF_4^-$, $C_6H_5SO_3^-$, p-CH$_3$—C$_6$H$_5$SO$_3^-$, HSO$_4^-$, PF$_6^-$, CF$_3$SO$_3^-$, in particular $F^-$, $Cl^-$, $Br^-$, $I^-$, $HF_2^-$, $BF_4^-$.

The compound of the formula III is advantageously used in an amount of from 0.5 to 35, in particular from 1 to 30, preferably from 3 to 25, percent by weight, based on the compound containing halogen which can be replaced by fluorine.

So as not to be tied exclusively to the abovementioned percentages by weight, it is possible in many cases to use the compound of the formula III in an amount of from 0.1 to 5 mol %, in particular from 0.4 to 2 mol %, preferably from 0.5 to 1 mol %, based on the compound which contains halogen capable of being replaced by fluorine. These amounts have been found to be sufficient in most cases.

Compounds of the formula III which can be used particularly successfully in the process of the invention include, inter-alia,
tetrakis(dimethylamino)phosphonium chloride,
tetrakis(dimethylamino)phosphonium bromide,
tetrakis(diethylamino)phosphonium chloride,
tetrakis(diethylamino)phosphonium bromide,
tetrakis(dipropylamino)phosphonium chloride,
tetrakis(dipropylamino)phosphonium bromide,
tetrakis(dibutylamino)phosphonium chloride,
tetrakis(dibutylamino)phosphonium bromide,
tetrakis(pyrrolidino)phosphonium chloride,
tetrakis(pyrrolidino)phosphonium bromide,
tetrakis(piperidino)phosphonium chloride,
tetrakis(piperidino)phosphonium bromide,
tetrakis(morpholino)phosphonium chloride,
tetrakis(morpholino)phosphonium bromide,
tris(dimethylamino)(diethylamino)phosphonium chloride,
tris(dimethylamino)(diethylamino)phosphonium bromide,
tris(dimethylamino)(dipropylamino)phosphonium chloride,
tris(dimethylamino)(dipropylamino)phosphonium bromide,
tris(dimethylamino)(dibutylamino)phosphonium chloride,
tris(dimethylamino)(dibutylamino)phosphonium bromide,
tris(dimethylamino)(dihexylamino)phosphonium chloride,
tris(dimethylamino)(dihexylamino)phosphonium bromide,
tris(dimethylamino)(diheptylamino)phosphonium chloride,
tris(dimethylamino)(diheptylamino)phosphonium bromide,
tris(dimethylamino)(cyclopentylamino)phosphonium chloride,
tris(dimethylamino)(cyclopentylamino)phosphonium bromide,
tris(dimethylamino)(cyclohexylamino)phosphonium chloride,
tris(dimethylamino)(cyclohexylamino)phosphonium bromide,
tris(dimethylamino)(diallylamino)phosphonium chloride,
tris(dimethylamino)(diallylamino)phosphonium bromide,
tris(diethylamino)(dimethylamino)phosphonium chloride,
tris(diethylamino)(dimethylamino)phosphonium bromide,
tris(diethylamino)(dihexylamino)phosphonium chloride,
tris(diethylamino)(dihexylamino)phosphonium bromide,
tris(diethylamino)(diheptylamino)phosphonium chloride,
tris(diethylamino)(diheptylamino)phosphonium bromide,
tris(piperidino)(diallylamino)phosphonium chloride,
tris(piperidino)(diallylamino)phosphonium bromide,
tris(pyrrolidino)(ethylmethylamino)phosphonium chloride,
tris(pyrrolidino)(ethylmethylamino)phosphonium bromide,
tris(pyrrolidino)(diethylamino)phosphonium chloride and/or
tris(pyrrolidino)(diethylamino)phosphonium bromide.

The catalyst used can be a compound of the formula III or a mixture of two or more compounds of the formula III. It is particularly convenient to use mixtures of compounds of the formula III as are obtained in the synthesis.

The process of the invention can be carried out in the presence or absence of a solvent. If solvents are used, both dipolar aprotic and aprotic as well as protic solvents are suitable.

Suitable dipolar aprotic solvents are, for example, dimethyl sulfoxide (DMSO), dimethyl sulfone, sulfolane (TMS), dimethylformamide (DMF), dimethylacetamide, 1,3-dimethylimidazolin-2-one, N-methylpyrrolidone, hexamethylphosphoramide, acetonitrile and/or benzonitrile. These solvents are employed alone or as a mixture of two or more of them.

Suitable aprotic solvents without a pronounced dipolar character include, inter alia, hydrocarbons or chlorinated hydrocarbons, for example benzene, toluene, ortho-xylene, meta-xylene, para-xylene, industrial mixtures of isomeric xylenes, ethylbenzene, mesitylene, ortho-chlorotoluene, meta-chlorotoluene, para-chlorotoluene, ortho-dichlorobenzene, meta-dichlorobenzene, para-dichlorobenzene or mixtures of one or more of these solvents.

The aprotic or dipolar aprotic solvent can be used in any amounts, for example from 5 to 500% by weight based on the substrate. However, preference is given to small amounts in the range from 5 to 30% by weight, based on the compound containing halogen which can be replaced by fluorine. If protic solvents are used, the amounts employed are in the range from 0.1 to 5% by weight, preferably from 0.1 to 2% by weight, based on the substrate containing halogen which can be replaced by fluorine.

Preference is also given, in the process of the invention, to carrying out the fluorination by halogen exchange at temperatures in the range from about room temperature to the boiling point of the reaction medium, thus in many cases the solvent, or of the starting materials which are to be reacted, depending on which boiling point is lower.

In many cases it suffices to carry out the process of the invention at a temperature of from 60 to 250° C., in particular from 90 to 220° C., preferably from 120 to 200° C.

The reaction temperature, thus also depends on the type of compound containing halogen which can be replaced by fluorine. Thus, comparatively unreactive compounds generally require higher reaction temperatures while comparatively reactive starting compounds can be reacted successfully even at relatively low temperatures.

The same applies to the reaction times. Relatively unreactive starting materials usually require longer reaction times than do more reactive starting materials.

At this point, attention may, in particular, also be drawn to the fact that replacement of only one halogen atom is in general easier to carry out than replacement of two or more halogen atoms by fluorine. Double or multiple halogen-fluorine exchange generally requires, if it is at all possible, considerably more severe reaction conditions (higher reaction temperatures and longer reaction times) than single halogen-fluorine exchange.

The process of the invention can be performed either under reduced pressure or under atmospheric or superatmospheric pressure. This possibility is utilized, for example, by adding small amounts of a low-boiling aprotic solvent which forms an azeotrope with water, for example benzene, xylene, mesitylene, cyclohexane or toluene, to the reaction suspension before the beginning of the reaction. Subsequently, part of the solvent is removed again together with water from the reaction suspension by application of a reduced pressure. This procedure enables the reaction rate and the yield to be increased and also enables the formation of by-products to be minimized.

The compound of the formula III can be used in the absence or presence of atmospheric oxygen. Preference is given to working under protective gas, for example argon or nitrogen.

When carrying out the process of the invention, it also has to be ensured that the reaction mixture is mixed well during the entire reaction. Finally, the possibility of a continuous or discontinuous procedure should also be noted. On an industrial scale, preference is given to a continuous process.

After the fluorination, the reaction mixture can, as already indicated above, advantageously be worked up by fractionation of the reaction mixture by distillation, which makes it possible to isolate and recycle the solvents. For an aqueous work-up, the mixture is poured into an excess of water and the products obtained are filtered off or extracted with organic solvents.

The intrinsically particularly high efficiency of the compounds of the formulae III and IV used according to the invention can, if desired, be further improved by addition of catalytically active compounds, In general, all catalysts known for this purpose to those skilled in the art, e.g. from the above-cited references, can be used. Catalysts which can be used include, inter alia, quatenary ammonium, phosphonium and amidophosphonium salts, crown ethers, polyethylene glycols, etc.

The process of the invention is particularly advantageously carried out with addition of catalytically effective amounts of tetramethylammonium chloride, tetrabutylammonium chloride, tetrabutylphosphonium bromide, tetraphenylphosphonium bromide, tetrakis(diethylamino)phosphonium bromide, 18-crown-6, PEG 500 dimethyl ether.

The following examples and comparative examples serve to illustrate the invention without restricting the invention to the examples.

EXAMPLE 1

Preparation of 4-fluorobenzaldehyde From 4-chlorobenzaldehyde 140 g (1 mol) of 4-chlorobenzaldehyde, 58 g (1 mol) of potassium fluoride, 5 g of nitrobenzene and 7.98 g of tetrakis(diethylamino)phosphonium bromide (phase transfer catalyst) are placed in a 500 ml four-neck flask fitted with thermometer, anchor stirrer and reflux condenser with bubble counter. The mixture is subsequently heated while stirring to 190° C. and allowed to react for 20 hours. After the reaction is complete, the reaction mixture is allowed to cool, dissolved in chlorobenzene, insoluble constituents are filtered off and the product (4-fluorobenzaldehyde) is purified by fractional distillation under reduced pressure.

Yield: 77%

Selectivity: 93%

Benzaldehyde content: 0.01%

COMPARATIVE EXAMPLE 2

Preparation of 4-fluorobenzaldehyde From 4-chlorobenzaldehyde

The procedure of Example 1 is repeated but without addition of nitrobenzene.

Yield: 75%

Selectivity: 90%

Benzaldehyde content: 0.15%

EXAMPLE 3

Preparation of 2-fluorobenzonitrile From 2-chlorobenzonitrile 137.5 g (1 mol) of 2-chlorobenzonitrile, 58 g (1 mol) of potassium fluoride, 5 g of nitrobenzene, 7.98 g of tetrakis(diethylamino)phosphonium bromide (phase transfer catalyst) and 30 ml of sulfolane are placed in a 500 ml four-neck flask fitted with thermometer, anchor stirrer and reflux condenser with bubble counter. The mixture is subsequently heated while stirring to 190° C. and allowed to react for 20 hours. After the reaction is complete, the reaction mixture is allowed to cool, dissolved in chlorobenzene, insoluble constituents are filtered off and the product (2-fluorobenzonitrile) is purified by fractional distillation under reduced pressure.

Yield: 94%

Selectivity: 96%

Benzonitrile content: 0.1 %

COMPARATIVE EXAMPLE 4

Preparation of 2-fluorobenzonitrile From 2-chlorobenzonitrile

The procedure of Example 3 is repeated but without addition of nitrobenzene.

Yield: 92%

Selectivity: 94%

Benzonitrile content: 0.35%

EXAMPLE 5

Preparation of 2-fluorobenzonitrile From 2-chlorobenzonitrile

The procedure of Example 3 is repeated but using 2.5 g of bis(4-nitrophenyl)ether in place of the nitrobenzene.

Yield: 91 %

Benzonitrile content: 0.01 %

EXAMPLE 6

Preparation of 2,6-difluorobenzonitrile From 2,6-dichlorobenzonitrile 172 g (1 mol) of 2,6-dichlorobenzonitrile, 116 g (2 mol) of potassium fluoride, 3 g of 4-fluoronitrobenzene, 7.98 g of tetrakis(diethyl-amino)phosphonium bromide (phase transfer catalyst) and 90 ml of sulfolane are placed in a 500 ml four-neck flask fitted with thermometer, anchor stirrer and reflux condenser with bubble counter. The mixture is subsequently heated while stirring to 190° C. and allowed to react for 15 hours. After the reaction is complete, the reaction mixture is allowed to cool, dissolved in chlorobenzene, insoluble constituents are filtered off and the product (2,6-difluorobenzonitrile) is purified by fractional distillation under reduced pressure.

Yield: 91%
Selectivity: 96%
2-Fluorobenzonitrile content: 0.04%

COMPARATIVE EXAMPLE 7

Preparation of 2,6-difluorobenzonitrile From 2,6-dichlorobenzonitrile

The procedure of Example 6 is repeated but without 4-fluoronitrobenzene.

2-Fluorobenzonitrile content: 0.7%

COMPARATIVE EXAMPLE 8

As Described in JP 08092148 A2

Preparation of 4-fluorobenzaldehyde from 4-chlorobenzaldehyde

The procedure is as described in JP 08092148 A2.
Yield: 38.4%
Benzaldehyde content: 0.72%

EXAMPLE 9

Preparation of 4-fluorobenzaldehyde from 4-chlorobenzaldehyde

The procedure of Comparative Example 8 is repeated, but TPB=tetrakis(diethylamino)phosphonium bromide is used in place of TPPB=tetraphenylphosphonium bromide.

Yield: 48%
Selectivity: 85%
Benzaldehyde content: 0.18%

EXAMPLE 10

Preparation of 4-fluorobenzaldehyde from 4-chlorobenzaldehyde 140 g (1 mol) of 4-chlorobenzaldehyde, 58 g (1 mol) of potassium fluoride, 5 g of dimethyl sulfoxide and 7.98 g of tetrakis(diethylamino)phosphonium bromide (phase transfer catalyst) are placed in a 500 ml four-neck flask fitted with thermometer, anchor stirrer and reflux condenser with bubble counter. The mixture is subsequently heated while stirring to 190° C. and allowed to react for 20 hours. After the reaction is complete, the reaction mixture is allowed to cool, dissolved in chlorobenzene, insoluble constituents are filtered off and the product (4-fluorobenzaldehyde) is purified by fractional distillation under reduced pressure.

Yield: 74%
Selectivity: 90%
Benzaldehyde content: 0.013%

EXAMPLE 11

Preparation of 2-fluorobenzonitrile From 2-chlorobenzonitrile 137.5 g (1 mol) of 2-chlorobenzonitrile, 58 g (1 mol) of potassium fluoride, 5 g of phenyl methyl sulfoxide, 7.98 g of tetrakis(diethylamino)phosphonium bromide (phase transfer catalyst) and 30 ml of sulfolane are placed in a 500 ml four-neck flask fitted with thermometer, anchor stirrer and reflux condenser with bubble counter. The mixture is subsequently heated while stirring to 190° C. and allowed to react for 20 hours. After the reaction is complete, the reaction mixture is allowed to cool, dissolved in chlorobenzene, insoluble constituents are filtered off and the product (2-fluorobenzonitrile) is purified by fractional distillation under reduced pressure.

Yield: 90%
Selectivity: 93%
Benzonitrile content: 0.08%

EXAMPLE 12

Preparation of 2,6-difluorobenzonitrile From 2,6-dichlorobenzonitrile 172 g (1 mol) of 2,6-dichlorobenzonitrile, 116 g (2 mol) of potassium fluoride, 3 g of dimethyl sulfoxide, 7.98 g of tetrakis(diethylamino)phosphonium bromide (phase transfer catalyst) and 90 ml of sulfolane are placed in a 500 ml four-neck flask fitted with thermometer, anchor stirrer and reflux condenser with bubble counter. The mixture is subsequently heated while stirring to 190° C. and allowed to react for 20 hours. After the reaction is complete, the reaction mixture is allowed to cool, dissolved in chlorobenzene, insoluble constituents are filtered off and the product (2,6-difluorobenzonitrile) is purified by fractional distillation under reduced pressure.

Yield: 93%
Selectivity: 95%
2-Fluorobenzonitrile content: 0.01%

TABLE 1

| No. | Substrate | Product | Fluoride | Catalyst | Solvent | Additive | Time [h] | T [° C.] | Yield [%] | Selectivity [%] | Dehalogenated product [%] |
|---|---|---|---|---|---|---|---|---|---|---|---|
| 1 | CHO-C6H4-Cl | CHO-C6H4-F | 1 mol of KF | TPB | — | Nitrobenzene | 20 | 190 | 77 | 93 | 0.01 |

TABLE 1-continued

| No. | Substrate | Product | Fluoride | Catalyst | Solvent | Additive | Time [h] | T [° C.] | Yield [%] | Selectivity [%] | Dehalo-genated product [%] |
|---|---|---|---|---|---|---|---|---|---|---|---|
| 2 | 4-Cl-C6H4-CHO | 4-F-C6H4-CHO | 1 mol of KF | TPB | — | — | 20 | 190 | 75 | 90 | 0.15 |
| 3 | 2-Cl-C6H4-CN | 2-F-C6H4-CN | 1 mol of KF | TPB | Sulfolane | Nitrobenzene | 20 | 190 | 94 | 96 | 0.1 |
| 4 | 2-Cl-C6H4-CN | 2-F-C6H4-CN | 1 mol of KF | TPB | Sulfolane | — | 20 | 190 | 92 | 94 | 0.35 |
| 5 | 2-Cl-C6H4-CN | 2-F-C6H4-CN | 1 mol of KF | TPB | Sulfolane | Bis(4-nitro-phenyl)ether | 20 | 190 | 91 | | 0.01 |
| 6 | 2,6-Cl2-C6H3-CN | 2,6-F2-C6H3-CN | 2 mol of KF | TPB | Sulfolane | 4-Fluoro-nitrobenzene | 15 | 190 | 91 | 96 | 0.04 |
| 7 | 2,6-Cl2-C6H3-CN | 2,6-F2-C6H3-CN | 2 mol of KF | TPB | Sulfolane | — | 15 | 190 | | | 0.7 |
| 8 | 4-Cl-C6H4-CHO | 4-F-C6H4-CHO | 1 mol of KF | TPPB | Sulfolane | Nitrobenzene | 3 | 215 | 38.4 | 69 | 0.72 |
| 9 | 4-Cl-C6H4-CHO | 4-F-C6H4-CHO | 1 mol of KF | TPB | Sulfolane | Nitrobenzene | 3 | 215 | 51 | 85 | 0.15 |

TABLE 1-continued

| No. | Substrate | Product | Fluoride | Catalyst | Solvent | Additive | Time [h] | T [°C.] | Yield [%] | Selectivity [%] | Dehalogenated product [%] |
|---|---|---|---|---|---|---|---|---|---|---|---|
| 10 | 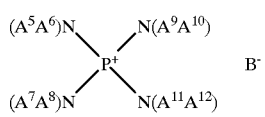 | 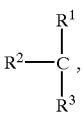 | 1 mol of KF | TPB | — | DMSO | 20 | 190 | 74 | 90 | 0.013 |
| 11 |  |  | 1 mol of KF | TPB | Sulfolane | Phenyl methyl sulfoxide | 20 | 190 | 90 | 93 | 0.08 |
| 12 | 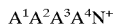 |  | 2 mol of KF | TPB | Sulfolane | DMSO | 15 | 190 | 93 | 95 | 0.01 |

TPB = Tetrakis(diethylamino)phosphonium bromide;
DMSO = Dimethyl sulfoxide;
TPPB = Tetraphenylphosphonium bromide

What is claimed is:

1. A process for preparing fluorine-containing compounds, which comprises reacting a compound containing one or more halogen atoms which can be replaced by fluoride with a fluoride of the formula I or a mixture of fluorides of the formula I $$KAT^+F^-  \qquad (I)$$

where $KAT^+$ is an alkali metal ion, $NH_4^+$, an alkaline earth metal ion or a cation of the formula II $$A^1A^2A^3A^4N^+ \qquad (II)$$

where $A^1$, $A^2$, $A^3$, $A^4$ are, independently of one another, identical or different and are each straight-chain or branched alkyl or alkenyl having from 1 to 12 carbon atoms, cycloalkyl having from 4 to 8 carbon atoms, aryl having from 6 to 12 carbon atoms or aralkyl having from 7 to 12 carbon atoms, in the presence of a compound or a mixture of compounds of the formula III $$(A^5A^6)N{\diagdown}{\atop}{\diagup}N(A^9A^{10}) \atop (A^7A^8)N{\diagup}P^+{\diagdown}N(A^{11}A^{12})\quad B^- \qquad (III)$$

where $A^5$, $A^6$, $A^7$, $A^8$, $A^9$, $A^{10}$, $A^{11}$, $A^{12}$ are, independently of one another, identical or different and are each straight-chain or branched alkyl or alkenyl having from 1 to 12 carbon atoms, cycloalkyl having from 4 to 8 carbon atoms, aryl having from 6 to 12 carbon atoms, aralkyl having from 7 to 12 carbon atoms, or $A^5A^6$, $A^7A^8$, $A^9A^{10}$, $A^{11}A^{12}$ are, independently of one another, identical or different and are bound to one another either directly or via O or N—$A^{13}$ to form a ring having from 3 to 7 ring atoms, $A^{13}$ is alkyl having from 1 to 4 carbon atoms and $B^-$ is a monovalent acid anion or the equivalent of a polyvalent acid anion, and in the presence of one or more compounds of the formulae IV encompassing IVa and/or IVb $$X—NO_2 \qquad (IVa),$$

$$X—SO—X' \qquad (IVb),$$

where X and X' are, independently of one another, identical or different and are each substituted or unsubstituted $(C_6–C_{18})$-aryl, substituted or unsubstituted $(C_5–C_{18})$-aryloxy, substituted or unsubstituted $(C_5–C_{18})$-arylthio, substituted or unsubstituted $(C_7–C_{12})$-aralkyl or a radical of the formula V $$R^2—\underset{R^3}{\overset{R^1}{\underset{|}{\overset{|}{C}}}}, \qquad (V)$$

where $R^1$, $R^2$, $R^3$ are, independently of one another, identical or different and are each hydrogen, straight-chain or branched alkyl or alkenyl having from 1 to 12 carbon atoms or cycloalkyl having from 4 to 8 carbon atoms, in the presence or absence of a solvent at temperatures in the range from 40° C. to 260° C.

2. The process as claimed in claim 1, wherein the fluorination by halogen exchange is carried out in the presence of nitrobenzene, 2-fluoronitrobenzene, 3-fluoronitrobenzene, 4-fluoronitrobenzene, 2,4-difluoronitrobenzene, 3-chloronitrobenzene, 2-nitrotoluene, 3-nitrotoluene, 4-nitrotoluene, 2-nitroanisole, 3-nitroanisole, 4-nitroanisole, 2-nitrothiophene, 4-nitro-2-propylbenzene, 1-nitronaphthalene, 2-nitronaphthalene, 2,4-dinitrobiphenyl, 4,4'-dinitrobiphenyl, bis(4-nitrophenyl) ether, bis(nitrophenyl)disulfide, nitromethane, nitroethane, nitropropane, nitroanthracene, 1-nitropyrene, dimethyl sulfoxide, diphenyl sulfoxide, phenyl methyl sulfoxide, diethyl sulfoxide and/or methyl trifluoromethyl sulfoxide.

3. The process as claimed in claim 1, wherein the fluorination by halogen exchange is carded out in the presence of nitrobenzene and/or DMSO.

4. The process as claimed in claim 1 wherein the compound of the formulae IVa and/or IVb is used in an amount of from 0.1 to 20% by weight, based on the compound containing halogen to be replaced.

5. The process as claimed in claim 1 wherein the compound of the formulae IVa and/or IVb is used in an amount of from 0.5 to 10% by weight, based on the compound containing halogen to be replaced.

6. The process as claimed in claim 1 wherein the compound containing halogen which can be replaced by fluorine is an aromatic compound having from 0 to 3 nitrogen atoms in the ring and substituted on the ring by chlorine or bromine substituents, which can be replaced by fluorine and may be substituted on the ring by at least one further substituent which promotes nucleophilic substitution of aromatic compounds.

7. The process as claimed in claim 1 wherein the starting compound containing one or more halogen atoms which can be replaced by fluorine is a compound of the benzene, naphthalene, pyridine, anthracene, phenanthrene, pyrimidine, pyrazine, quinoline, isoquinoline, acridine, acridone, cinnoline, phthalazine, quinazoline, quinoxaline, phenazine and/or phenoxazine type.

8. The process as claimed in claim 1 wherein the compound containing one or more halogen atoms which can be replaced by fluorine is a substituted benzaldehyde or benzonitrile.

9. The process as claimed in claim 1 wherein the compound of the formula I which is used is potassium fluoride and/or cesium fluoride.

10. The process as claimed in claim 1 wherein the compound of the formula I which is used is tetramethylammonium fluoride and/or tetraphenylammonium fluoride.

11. The process as claimed in claim 1 wherein from 0.5 to 10 molar equivalents of compound of the formula I are used per molar equivalent of halogen atoms to be replaced.

12. The process as claimed in claim 1 wherein from 1 to 2 molar equivalents of compound of the formula I are used per molar equivalent of halogen atoms to be replaced.

13. The process as claimed in claim 1 wherein the fluorination by halogen exchange is carried out in the presence of a compound of the formula III in which $A^5, A^6, A^7, A^8, A^9, A^{10}, A^{11}, A^{12}$ are, independently of one another, identical or different and are each straight-chain or branched alkyl or alkenyl having from 1 to 12 carbon atoms or cycloalkyl having from 4 to 8 carbon atoms.

14. The process as claimed in claim 1 wherein the fluorination by halogen exchange is carried out in the presence of a compound of the formula III in which $A^5, A^6, A^7, A^8, A^9, A^{10}, A^{11}, A^{12}$ are, independently of one another, identical or different and are each straight-chain or branched alkyl or alkenyl having from 1 to 8 carbon atoms or cycloalkyl having 5 or 6 carbon atoms.

15. The process as claimed in claim 1 wherein the fluorination by halogen exchange is carried out in the presence of a compound of the formula III in which $A^5, A^6, A^7, A^8, A^9, A^{10}, A^{11}, A^{12}$ are, independently of one another, identical or different and are each straight-chain or branched alkyl having from 1 to 4 carbon atoms.

16. The process as claimed in claim 1 wherein in the compound of the formula III $A^5A^6=A^7A^8$ or $A^5A^6=A^7A^8=A^9A^{10}$ or $A^5A^6=A^7A^8=A^9A^{10}=A^{11}A^{12}$.

17. The process as claimed in claim 1 wherein in the compound of the formula III $A^5=A^6=A^7=A^8$ or $A^5=A^6=A^7=A^8=A^9=A^{10}$ or $A^5=A^6=A^7=A^8=A^9=A^{10}=A^{11}=A^{12}$.

18. The process as claimed in claim 1 wherein in the compound of the formula III $A^5A^6$ or $A^5A^6$ and $A^7A^8$ or $A^5A^6$ and $A^7A^8$ and $A^9A^{10}$ or $A^5A^6$ and $A^7A^8$ and $A^9A^{10}$ and $A^{11}A^{12}$ are joined to one another either directly or via O or N—$A^{13}$ to form a saturated or unsaturated ring having 5 or 6 ring atoms.

19. The process as claimed in claim 1 wherein in the compound of the formula III $A^5A^6$ or $A^7A^8$ and $A^9A^{10}$ or $A^5A^6$ and $A^7A^8$ and $A^9A^{10}$ or $A^5A^6$ and $A^7A^8$ and $A^9A^{10}$ and $A^{11}A^{12}$ are joined to form a ring including, as ring members, the N atom on which the respective radicals $A^5$ to $A^{12}$ are located and optionally O or N—$A^{13}$ and $CH_2$ groups.

20. The process as claimed in claim 1 wherein in the compound of the formula III $B^-$ is $F^-$, $Cl^-$, $Br^-$, $I^-$, $HF_2^-$, $BF_4^-$, $C_6H_5SO_3^-$, p-$CH_3$—$C_6H_5SO_3^-$, $HSO_4^-$, $PF_6^-$ or $CF_3SO_3^-$.

21. The process as claimed in claim 1 wherein in the compound of the formula III $B^-$ is $F^-$, $Cl^-$, $Br^-$, $I^-$, $HF_2^-$ or $BF_4^-$.

22. The process as claimed in claim 1 wherein the compound of the formula III is used in an amount of from 0.5 to 35% by weight, based on the compound containing halogen which can be replaced by fluorine.

23. The process as claimed in claim 1 wherein a dipolar aprotic, an aprotic or a protic solvent is used.

24. The process as claimed in claim 1 wherein dimethyl sulfoxide, dimethyl sulfone, sulfolane, dimethylformamide, dimethylacetamide, 1,3-dimethylimidazolin-2-one, N-methylpyrrolidone, hexamethylphosphoramide, acetonitrile, benzonitrile or a mixture of these is used as dipolar aprotic solvent.

25. The process as claimed in claim 1 wherein an aromatic hydrocarbon, a chlorinated aromatic hydrocarbon or a mixture of these is used as aprotic solvent.

26. The process as claimed in claim 25, wherein benzene, toluene, ortho-xylene, meta-xylene, para-xylene, an industrial mixture of isomeric xylenes, ethylbenzene, mesitylene, ortho-chlorotoluene, meta-chlorotoluene, para-chlorotoluene, ortho-dichlorobenzene, meta-dichlorobenzene, para-dichlorobenzene or a mixture of these is used as aprotic solvent.

27. The process as claimed in claim 1 wherein the reaction is carried out at from 60 to 250° C.

28. The process as claimed in claim 1 wherein the reaction is carried out at from 90 to 220° C.

29. The process as claimed in claim 1 wherein the reaction is carried out at from 120 to 200° C.

30. The process as claimed in claim 1, wherein the compound of the formulae IVa and/or IVb is used in an amount of from 1 to 5% by weight, based on the compound containing halogen to be replaced.

* * * * *